(12) United States Patent
Aranda et al.

(10) Patent No.: US 9,434,899 B2
(45) Date of Patent: Sep. 6, 2016

(54) HYDROESTERIFICATION PROCESS FOR PRODUCING BIODIESEL FROM WET MICROALGAE BIOMASS

(71) Applicants: PETROLEO BRASILEIRO S.A.-PETROBRAS, Rio de Janeiro, RJ (BR); UNIVERSIDADE FEDERAL DO RIO DE JANEIRO-UFRJ, Rio de Janeiro, RJ (BR)

(72) Inventors: Donato Alexandre Gomes Aranda, Rio de Janeiro (BR); Yordanka Reyes Cruz, Rio de Janeiro (BR); Gisel Chenard Dias, Rio de Janeiro (BR); Leonardo Brantes Bacellar Mendes, Rio de Janeiro (BR); Rafael Richard Joao, Rio de Janeiro (BR)

(73) Assignees: PETROLEO BRASILEIRO S.A—PETROBRAS, Rio de Janeiro (BR); UNIVERSIDADE FEDERAL DO RIO DE JANEIRO—UFRJ, Rio de Janeiro (BR)

( * ) Notice: Subject to any disclaimer, the term of this patent is extended or adjusted under 35 U.S.C. 154(b) by 22 days.

(21) Appl. No.: 14/379,369

(22) PCT Filed: Nov. 28, 2012

(86) PCT No.: PCT/BR2012/000479
§ 371 (c)(1),
(2) Date: Aug. 18, 2014

(87) PCT Pub. No.: WO2014/082143
PCT Pub. Date: Jun. 5, 2014

(65) Prior Publication Data
US 2015/0240173 A1    Aug. 27, 2015

(51) Int. Cl.
| | |
|---|---|
| *C07C 67/08* | (2006.01) |
| *C10L 1/02* | (2006.01) |
| *C07C 51/09* | (2006.01) |
| *C11C 1/04* | (2006.01) |
| *C11C 3/00* | (2006.01) |

(52) U.S. Cl.
CPC ............. *C10L 1/026* (2013.01); *C07C 51/09* (2013.01); *C07C 67/08* (2013.01); *C11C 1/04* (2013.01); *C11C 3/003* (2013.01); *C10L 2200/0476* (2013.01); *C10L 2290/06* (2013.01); *C10L 2290/08* (2013.01); *C10L 2290/10* (2013.01); *C10L 2290/543* (2013.01); *Y02E 50/13* (2013.01); *Y02P 20/127* (2015.11)

(58) Field of Classification Search
None
See application file for complete search history.

(56) References Cited

U.S. PATENT DOCUMENTS

| | | | |
|---|---|---|---|
| 2009/0081742 | A1 | 3/2009 | Dunlop et al. |
| 2011/0092725 | A1 | 4/2011 | Jones |
| 2011/0189741 | A1 | 8/2011 | Echevarria Parres |

OTHER PUBLICATIONS

Almarales et al., Hydroesterification of Nannochloropsis oculata microalga's biomass to biodiesel on Al2O3 supported Nb2O5 catalyst, Natural Science vol. 4, No. 4, 204-210 (2012).*
International Search Report for PCT/BR2012/000479, dated Apr. 3, 2013.

* cited by examiner

*Primary Examiner* — Suzanne M Noakes
*Assistant Examiner* — Stephen Chong
(74) *Attorney, Agent, or Firm* — Sughrue Mion, PLLC

(57) ABSTRACT

The invention relates to the preparation of carboxylic acid esters compounds, biodiesel (B) from microalgae, for use as a biofuel for compression type ignition. The objective is achieved through a hydroesterification process of a microalgae biomass (MU) comprising a hydrolysis stage and the esterification stage by means of heterogeneous catalysis. The wet microalgae biomass (MU) is the result of a process of cultivation concentration and is hydrolyzed directly in a hydrolysis column (20). Fatty acids (C), water (A) and raw glycerin (G) are obtained following the hydrolysis. The fatty acids (C) are esterified by reactive distillation in the presence of an impregnated heterogeneous catalyst (I).

5 Claims, 4 Drawing Sheets

HYDROESTERIFICATION PROCESS FOR PRODUCING BIODIESEL FROM WET MICROALGAE BIOMASS

CROSS REFERENCE TO RELATED APPLICATIONS

This application is a National Stage of International Application No. PCT/BR2012/000479, filed Nov. 28, 2012, the contents of all of which are incorporated herein by reference in their entirety.

FIELD OF THE INVENTION

The field of application of the present invention is among the processes for the preparation of compounds of carboxylic acid esters from microalgae, for use as a biofuel for compression type ignition.

THE BASIS OF THE INVENTION

The methyl and ethyl esters of fatty acids, biodiesel, are produced from vegetable oils and animal fats through various processes. Among these processes, transesterification using an alkali, such as KOH as the catalyst is particularly noteworthy. This process generates high levels of conversion of triglycerides into methyl esters in a short reaction time. For this reason, it is the most commercially used process for producing biofuels from vegetable oils and animal fat.

One of the major problems encountered in the production of biodiesel by the transesterification method is the acquisition of raw materials, which must have low acidity and low moisture content, characteristic of oils refined from oleaginous plants, which restricts the method to a small range of raw materials, which are largely quite expensive.

Moreover, the process is carried out in the presence of homogeneous alkaline catalysts, which despite favoring high yields, cause the formation of soap in the product and a difficult stage of separation between ester and glycerin.

In another process, hydrolysis followed by esterification, also known as hydroesterification, also falls within this context, as an alternative to the conventional process of transesterification for producing biodiesel.

Acid hydrolysis favors the complete transformation of the triglycerides present in low acidity oils, into free fatty acids, which can be esterified to form esters. Hydrolysis can also be performed from any raw material, such as oils from oleaginous plants, greasy industrial waste, frying oils and even acidic sludge from the refining of vegetable oils, regardless of the content of free fatty acids and moisture found.

Studies indicate that microalgae, rich in lipids, could have potential for use as feedstock in the production of biofuels.

Microalgae belong to a group of hundreds of species, which comprise the basis of the food chain, fix a large amount of carbon dioxide while they produce and sustain atmospheric oxygen.

Productivity values of 50,000 liters of oil/ha-year from algae are common in the literature, close to fifteen times greater than that from palm, a high productivity oilseed. These oils have numerous applications; however, it is particularly noteworthy that oils from microalgae are similar to vegetable and fish oils and may be considered to be potentials substitutes for petroleum products.

The idea of using oils from microalgae for fuel production has been suggested for more than 50 years, at least. Algae biomass fermentative processes for producing methanol and ethanol were among the first uses.

Studies on the effective capacity of microalgae serving as feedstock for biodiesel production are scarce and this line of research is still in its infancy, requiring a great deal of research and development.

However, high energy consumption, primarily in the stages of concentration and drying of biomass, together with the insufficient information on the techniques of oil extraction, are limiting factors in the application of algal biomass for the production of biodiesel, particularly from the point of view of sustainability and economic viability of the available technologies.

Document U.S. 2011/0092725 A1 describes a process for the hydrolysis of oils and fats, which is presented as a pre-treatment for an esterification stage by heterogeneous catalysis in a fixed bed reactor, for the production of biofuels, detergents, soaps or solvents. Animal fat, vegetable oil, acidified oil, recycled cooking oil and/or algae oil can be used as feedstock. When algae oil is used, a stage for preparation of the biomass is necessary, wherein the oil is extracted for subsequent use in the process.

Document U.S. 2009/0081742 A1 presents the equipment and process for producing biodiesel from algae oil. After the concentration of biomass, the fracturing (hydrolysis) of cells for extracting the oil is processed.

This extracted oil is fed into a machine, which also receives ethanol or alternatively methanol, where a reaction takes place to produce biodiesel and glycerin. This mixture of biodiesel and glycerin is then conveyed to subsequent separation and purification processes.

U.S. 2011/0189741 A1 discloses a process for extracting algae lipids and their transesterification for the production of biodiesel. Ultrasound is applied as the agent for fracturing the cell walls of the algae.

The oil is extracted and following a transesterification reaction, biodiesel is generated in an admixture with glycerin. This mixture of biodiesel and glycerin is then conveyed to separation and subsequent purification processes.

Based on what has been deduced from the representative examples of the prior art, the preparation of compounds of fatty acids esters from microalgae exhibits a field for multiple variations within the inventive concept.

According to the documents presented herein, the described processes are characterized by having a stage of preparation of the biomass, consisting of the extraction of the oil, so as to enable its use in these processes, and can produce biodiesel mixed with glycerin, requiring a further separation stage.

SUMMARY OF THE INVENTION

The objective of this invention is a process for producing biodiesel from wet microalgae biomass.

The objective is achieved through a process of hydroesterification of a microalgae biomass comprising a hydrolysis stage and an esterification stage by means of heterogeneous catalysis. A wet microalgae biomass resulting from a cultivation concentration process is used as the feedstock, which is directly hydrolyzed in a distillation column. Water and glycerin at the base of the column and fatty acid at the top are obtained.

Fatty acids are esterified in a second reactive distillation column, called the esterification column, using a niobium oxide catalyst impregnated with phosphoric acid and a reagent that can be selected from methanol and ethanol.

High purity methyl or ethyl ester is obtained following esterification. The actual alcohol present neutralizes the acidity.

The process of the invention provides as an end product a biodiesel with a high degree of purity and, additionally, as there are no washing stages, the process does not generate a large amount of effluents or high consumption of adjuvant chemical compounds.

BRIEF DESCRIPTION OF THE FIGURES

The characteristics of the hydroesterification process for producing biodiesel from wet microalgae biomass, subject of this invention, will be better understood from the detailed description that follows, as a mere example, associated with the below-referenced drawings, which are an integral part of this report.

DETAILED DESCRIPTION OF THE INVENTION

Figure 1:
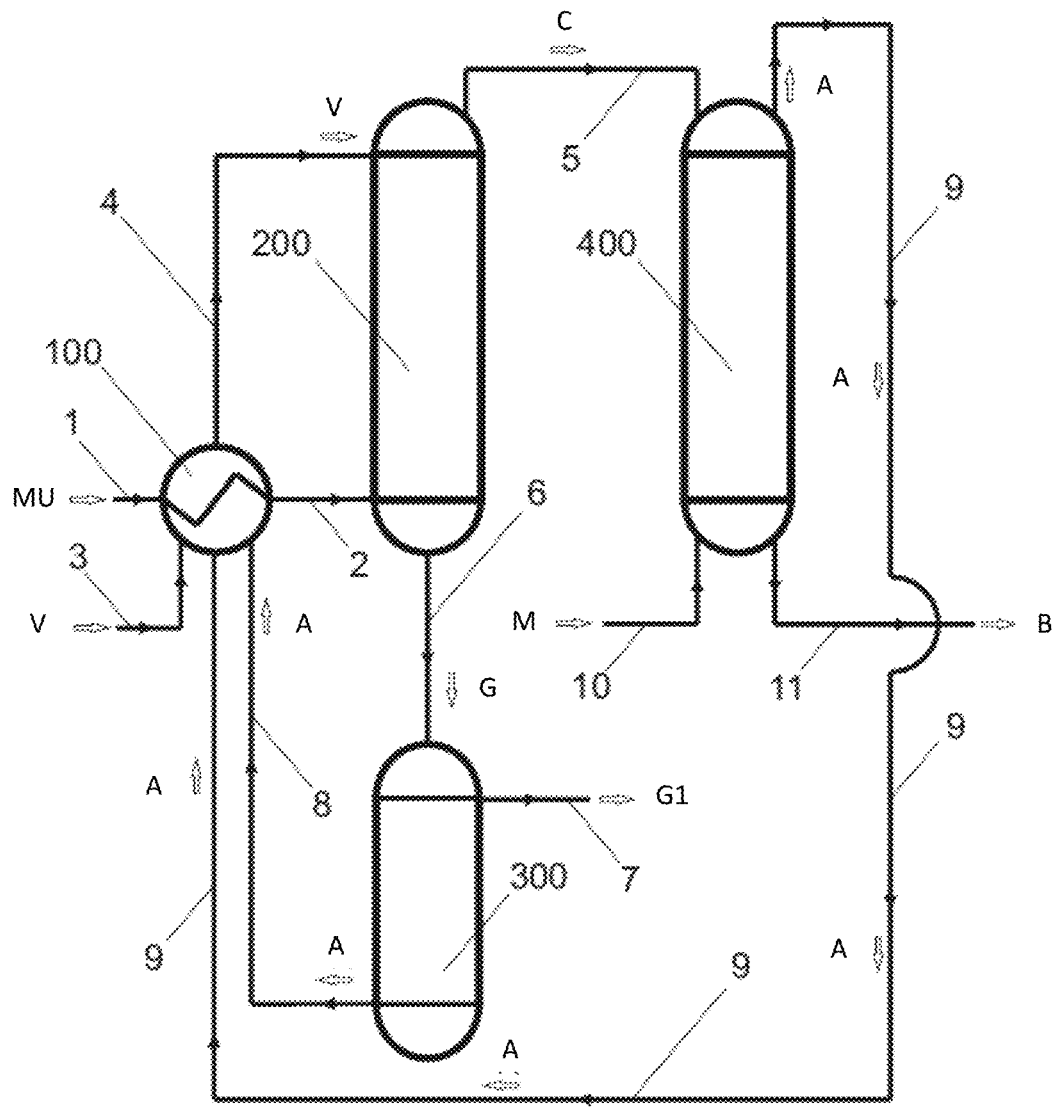
FIG. 1 is a schematic representation of the hydroesterification process according to the invention.

The present invention relates to the production of biodiesel (B) from wet microalgae biomass (MU) by means of a hydroesterification process according to a preferred embodiment of the invention, which may be followed with the help of FIG. 1.

The reactions involved in the process are represented below:

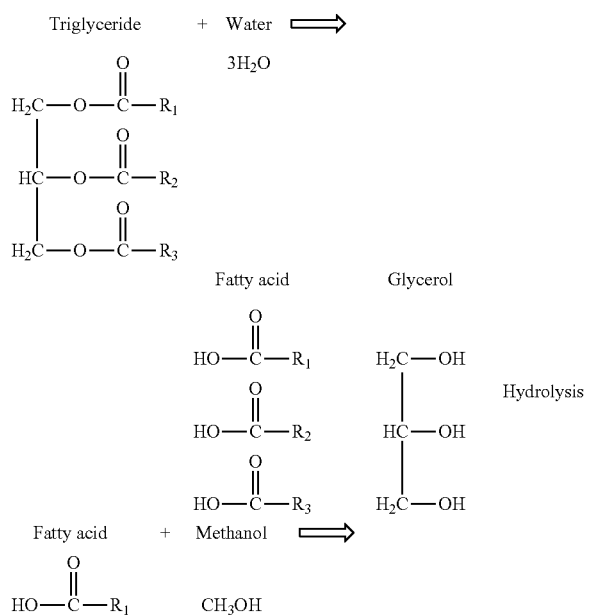

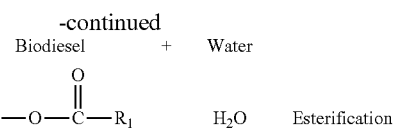

Thus, the process of the invention comprises the following stages:

A first hydrolysis stage in which the chemical reaction takes place between the wet microalgae biomass (MU) and water in the vapor state (V), generating as products raw glycerin (G) and fatty acids (C) and which in turn comprises the following steps:

Feed wet microalgae biomass (MU) through a first supply line (1) to a heat exchange device (100) for heating by means of steam (V) coming from a source external to this heat exchange device (100) through a first steam line (3);

Introduce wet microalgae biomass (MU) heated at the bottom of a hydrolysis column (20) through a second supply line (2) coming from the heat exchange device (100);

Introduce steam (V) into the top of the hydrolysis column (20), so that the hydrolysis reaction occurs and results in raw glycerin (G) and fatty acid (C), through a second steam line (4) from the heat exchange unit (100);

Remove fatty acid (C) from the top of the hydrolysis column (200) through a first product line (5);

Remove raw glycerin (G) from the bottom of the hydrolysis column through a second product line (6);

Introduce into a separator (300) the raw glycerin (G) from the second product line (5), so that water (A) is separated;

Recycle the water (A) separated in separator (300) through a first recycling line (8) to heat exchange device (100) wherein the water (A) is transformed into steam (V) and reintroduced into the hydrolysis column (200) along with the steam (V) coming from an external source;

Remove common glycerin (G1) from the separator (300) through a third product line (7); and A second esterification stage in which a chemical reaction occurs between the fatty acids (C) produced in the first hydrolysis stage and a reagent (R) that can be selected from methanol (M) and ethanol (E), result in the production of biodiesel (B) and water (A), and which in turn comprises the following steps:

Feed through the top of a esterification column (400), the fatty acid (C) produced during the hydrolysis stage and transported by the first product line (5);

Introduce through the bottom of the esterification column (400), by means of a third supply line (10) from an external source a reagent (R), so that in the presence of an impregnated heterogeneous catalyst (I) present inside the esterification column (400), the esterification reaction occurs and results in biodiesel (B) and water (A);

Recycle the water (A) produced during the esterification reaction to heat the exchange device (100) through a second recycling line (9) at the top of the esterification column (400), where the water (A) is transformed into steam (V) and reintroduced into the hydrolysis column (200) along with the steam (V) coming from an external source;

Remove the biodiesel (B) produced through the bottom of the esterification column (400) by means of a fourth product line (11).

The wet microalgae biomass (MU) used as feedstock is the result of a process of concentrating a cultivation of microalgae, preferably by centrifuging, producing at the end a wet microalgae biomass (MU) with a concentration in a range between 4% and 20%, and a lipid content in a range between 20% and 29%.

The wet microalgae biomass (MU) is hydrolyzed directly on a hydrolysis column (200), with a reaction temperature in a range between 180° C. and 300° C. for a time varying in the range between 0.5 h and 2 hours.

The hydrolysis comprises a chemical reaction between the wet algae biomass and water, from which fatty acids and raw glycerin are obtained. The hydrolysis generates a high acidity product. The product of the hydrolysis, the fatty acids (C), has an acidity greater than 99%.

Thus, instead of reducing the acidity through a refining of the extracted oil, the hydrolysis purposely increases the acidity of the feedstock.

The fatty acids (C) exit the hydrolysis column (200) at a temperature of approximately 260° C.

The esterification reaction is carried out at a temperature varying in the range between 110° C. and 250° C., for a time varying in the range from 0.5 to 2 hours. The reagent (R) used in the esterification reaction is preferably methanol (M).

The impregnated heterogeneous catalyst (I) present inside the esterification column (400) is a catalyst of niobium oxide impregnated with phosphoric acid, which differentiates it with respect to the catalysts used in the prior art.

The molar ratio between methanol (M) and the fatty acids (C) in the esterification reaction is in a value that varies in the range of 1.0 to 4.0.

The esterification reaction occurs simultaneously with a distillation inside the esterification column (400), so that the reaction is continuously moved, and is able to achieve almost complete conversion.

The methyl (or ethyl) ester produced exhibits a high purity, because the alcohol neutralizes the acid present and there is no possibility of contact between the biodiesel (B) and common glycerin (G1), since the latter is removed in advance during the hydrolysis stage, obviating the need for biodiesel (B) washing stages.

The process of the invention enables the use of any grease feedstock, such as animal fat, vegetable oil, used cooking oil, acid sludge from refining vegetable oils, among others, for the production of biodiesel (B), regardless of their acidity and moisture.

Only water is generated as a byproduct and is conveyed to the hydrolysis process. A high purity biodiesel is thus produced, without the need for washing stages.

The process of this invention reduces or even eliminates contamination problems related to biodiesel contamination produced by free or total glycerol waste (mono-, di-, and tri-glycerides).

Here following is an example illustrating the efficiency of the process of the invention:

Example 1

A wet microalgae biomass (B) of the species "Monoraphidium contortum," identified as MORF-1, was used in a trial of this process.

Fatty acids (C), produced from the hydrolysis reaction of this biomass, were esterified through reaction with methanol (M) using as a catalyst niobium oxide powder produced by CIA Mineira do Pirocloro de Araxá [Araxá Pyrochlore Mining CO.], CBMM, identified as HY-340, impregnated with phosphoric acid, to obtain biodiesel (B).

When the powder type pure niobium oxide catalyst of CBMM (HY-340) was initially used in the "in situ" hydroesterification of the wet microalgae biomass (B), it was noted that very low conversion values were obtained.

In the tests of this invention, a catalyst was prepared from niobium oxide impregnated with phosphoric acid and positive results were observed in terms of conversion values.

For this impregnation, a suspension was prepared by adding about 3 ml of aqueous solution of approximately 1 mol/L phosphoric acid for each gram of niobium oxide.

This suspension was agitated continuously for approximately 48 hours, for subsequent centrifuging, drying, and calcination at a temperature around 300° C. for a period of two hours.

The biomass was obtained in a photobioreactor and the reactions were conducted in an autoclave (batch) reactor of Parr Instruments Inc.—Stainless steel model 4842.

The MORF-1 biomass, used as feedstock is characterized by a moisture content between 80% and 96%, and a lipid content between 20% and 29% following centrifuging.

The operating conditions of the reactions are shown in Table 1 below:

TABLE 1

| Operating Conditions | Unit | Hydrolysis | Esterification |
|---|---|---|---|
| Temperature | ° C. | 180-300 | 110-250 |
| Biomass concentration | % | 4-20 | — |
| Catalyst concentration | % | — | 5-20 |
| Alcohol/fatty acid molar ratio | Mol | — | 1.0-4.0 |
| Reaction time | hrs | 0.5-2 | 0.5-2 |
| Agitation (RPM) | | 300-700 | 300-700 |

The methyl ester produced or biodiesel (B) of the microalgae "Monoraphidium contortum" was characterized in relation to some parameters required by the National Oil, Natural Gas and Biofuel Agency [Agencia Nacional de Petróleo] (ANP), based on the ANP Resolution No. 14, of May 5, 2012, as shown in Table 2 below.

As may be observed, the values of mono-, di- and tri-glycerides presented in Table 2 are lower than those specified in the ANP Resolution. This fact is associated with the obtaining of biodiesel (B) from free fatty acids (C) resulting from the hydrolysis.

It is known that among the vegetable oils, the fatty acid composition (C) varies and, thus, its physical-chemical properties as well, the same occurring with the various microalgae species and different cultivation conditions.

TABLE 2

| CHARACTERISTIC | METHOD | BIODIESEL SPECIFICATION B-100 | MICROALGAE BIODIESEL |
|---|---|---|---|
| Ester content, % w/w | EN 14103 | 96.5 min. | 99.06 |
| Free glycerol, % w/w | ASTM-D 6584/EN 14105/14106 | 0.02 max. | 0.00152 |
| Total glycerol, % w/w | ASTM-D 6584/EN 14105 | 0.25 max. | 0.0106 |
| Monoglycerides, % w/w | ASTM-D 6584/EN 14105 | 0.80 max. | 0.0310 |
| Diglycerides, % w/w | ASTM-D 6584/EN 14105 | 0.20 max. | 0.0000 |
| Triglycerides, % w/w | ASTM-D 6584/EN 14105 | 0.20 max. | 0.0097 |
| Oxidation stability at 110° C., h | EN 14112 | 6 h | 4.77 h |

Figure 2:
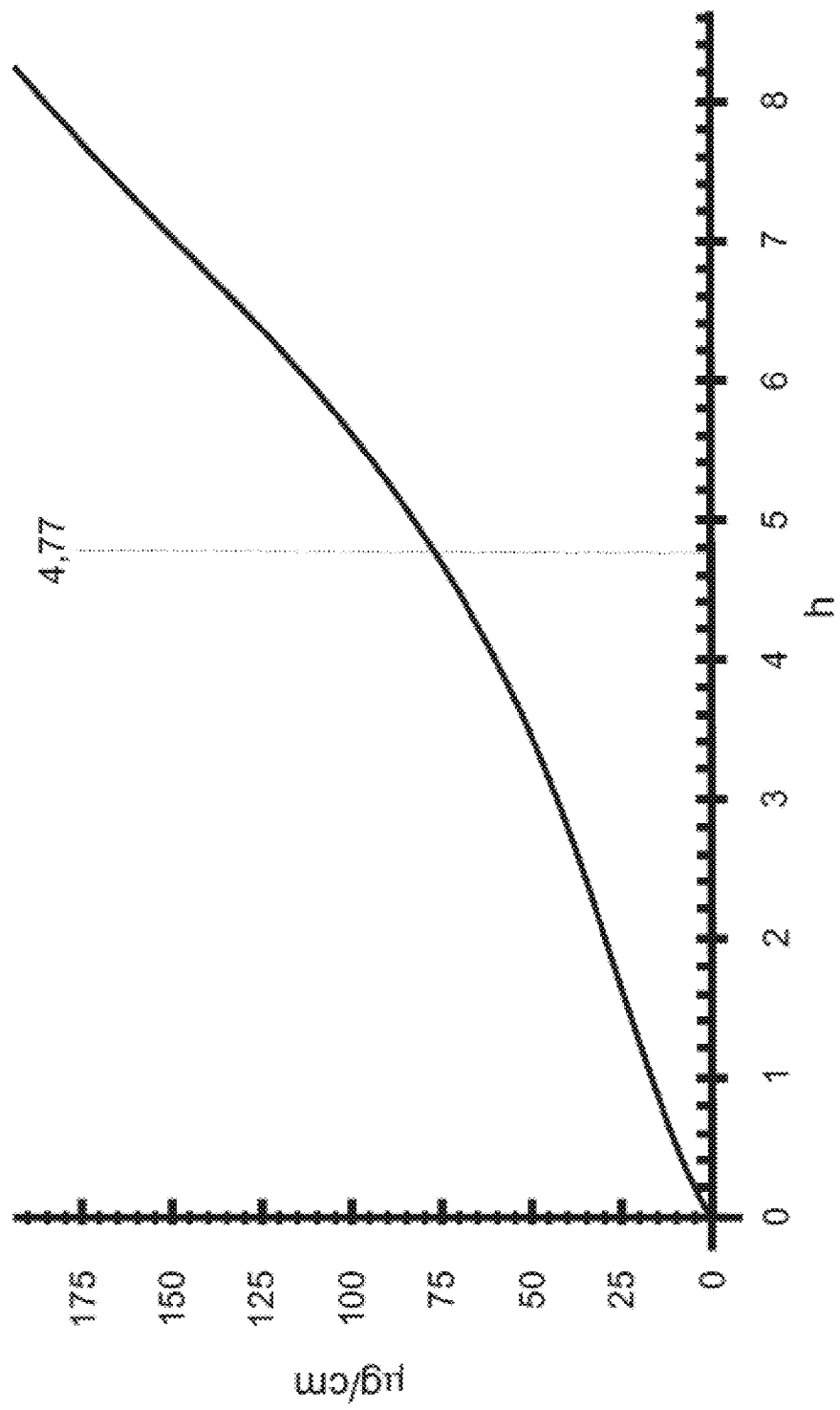
FIG. 2 is a representation of the oxidative stability of biodiesel produced from the "Monoraphidium contortum" microalgae.
Figure 3:
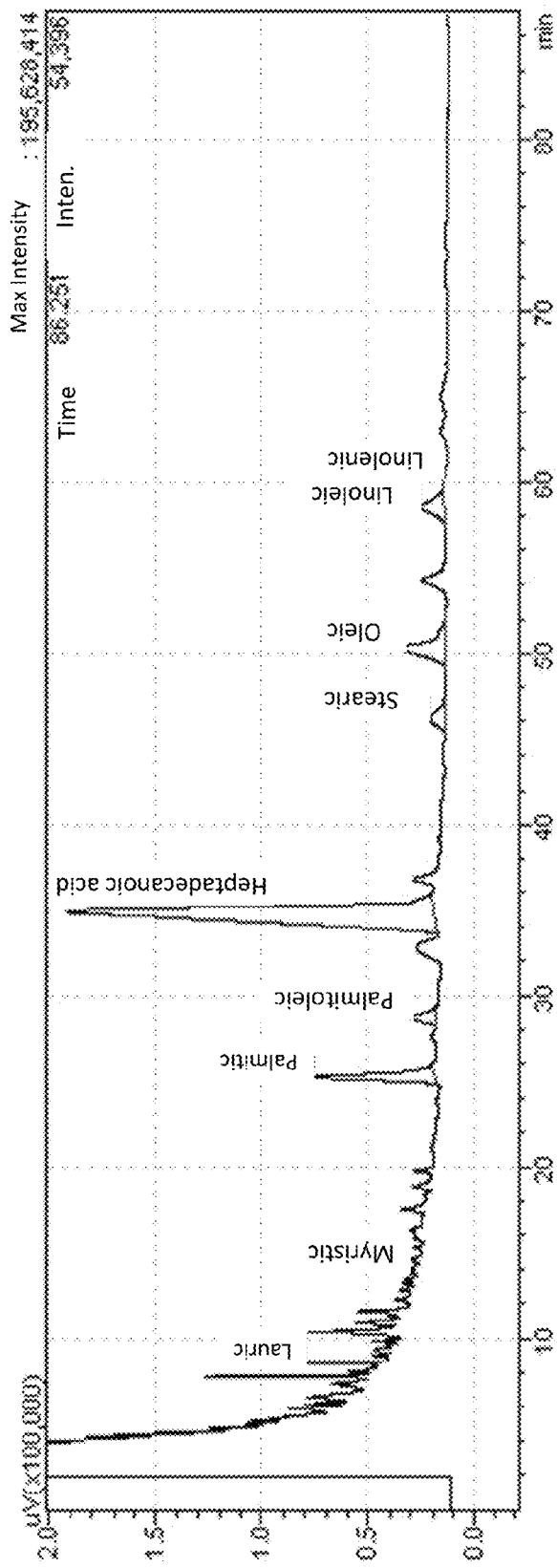
FIG. 3 is a representation of a chromatographic profile of fatty acids resulting from hydrolysis of the microalgae biomass.
Figure 4:
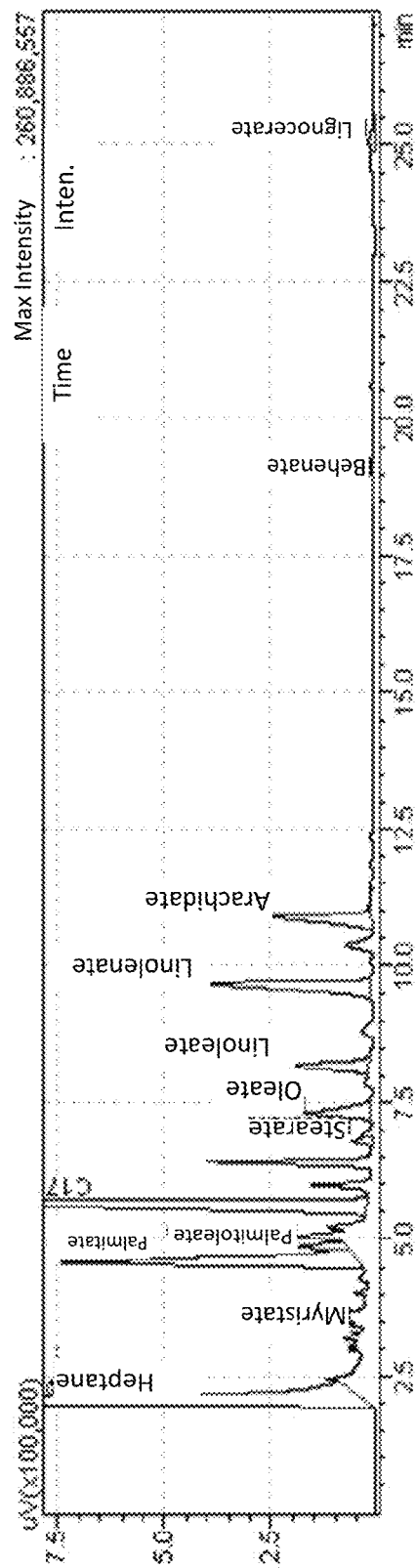
FIG. 4 is a representation of a chromatographic profile of esters/biodiesel resulting from esterification of the microalgae biomass.

The oxidation stability of the sample obtained according to the invention was about 4.77 hours, as per FIG. 2. This result corresponds to the results of the lipid profile of this sample, which has a high saturated fatty acid content (C) in the feedstock and, consequently, higher saturated ester content in the composition of the biodiesel (B), an aspect confirmed by the chromatography shown in FIGS. 3 and 4. The value obtained is not very different from the esters profiles typically found in conventional oilseeds, over a time of 6 hours for the soybean biodiesel (B) standard. Typically, antioxidant additives are added to increase oxidation stability.

According to these data, the species studied exhibited the following fatty acid (C) distribution: content of SAFA>PUFA>MUFA Where:
SAFA—Saturated fatty acids (C);
MUFA: Monounsaturated fatty acids (C), and
PUFA: Polysaturated fatty acids (C).

It is noted that higher values relate to SAFA's particularly C16:0 (palmitic acid) and C11:0 (undecanoic acid).

High levels of C18:3 (linolenic acid) were observed in relation to the PUFAs. The second highest content PUFA was C18:2 (linoleic acid).

As for the MUFA's C18:1 (oleic acid) stands out.

Therefore, the following advantages may be listed for the process of the invention in relation to existing procedures in the art:
- absence of the biomass drying stage by highly energy-intensive freeze-drying; and
- absence of the stage for extracting oil from the microalgae biomass which, depending on the method used, consumes chemical reagents, enzymes or the combination of both, in addition to consuming energy in the solvent evaporation process, resulting in a high operating cost.

Although the present invention has been described in its preferred embodiment, the main concept guiding the invention, which is a hydroesterification technology for the production of biodiesel (B) from wet microalgae biomass (MU), remains unchanged as to its innovative character, in that those normally skilled in the art may envision and apply variations, modifications, alterations, adaptations, and reasonable and compatible equivalents to the concerned work environment, without, however, departing from the spirit and the scope of the invention, which are represented by the claims that follow.

The invention claimed is:

1. A hydroesterification process for producing biodiesel from wet microalgae biomass, comprising:
a first hydrolysis stage in which a chemical reaction takes place, between the wet microalgae biomass (MU) and water in the vapor state (V), generating as products raw glycerin (G) and fatty acids (C) and which in turn comprises the following stages:
feeding wet microalgae biomass (MU) through a first supply line (1) to a heat exchange device (100) for heating by means of steam (V) coming from a source external to this heat exchange device (100) through a first steam line (3);
introducing wet microalgae biomass (MU) heated at the bottom of a hydrolysis column (200) through a second supply line (2) coming from the exchange device (100);
introducing steam (V) into the top of the hydrolysis column (200), so that a hydrolysis reaction occurs and results in raw glycerin (G) and fatty acid (C), through a second steam line (4) from heat exchange unit (100);
removing fatty acid (C) from the top of the hydrolysis column (200) through a first product line (5);
removing raw glycerin (G) from the bottom of the hydrolysis column through a second product line (6);
introducing into a separator (300) raw glycerin (G) from the second product line (5), so that water (A) is separated;
recycling the water (A) separated in the separator (300) through a first recycling line (8) to the heat exchange device (100) wherein the water (A) is transformed into steam (V) and reintroduced into the hydrolysis column (200) along with the steam (V) coming from an external source; and
removing common glycerin (G1) from the separator (300) through a third product line (7), and
a second esterification stage in which a chemical reaction takes place, between the fatty acids (C) produced in the first hydrolysis stage and a reagent (R) that can be selected from methanol (M) and ethanol (E), resulting in the production of biodiesel (B) and water (A) and which in turn comprises the following steps:
feeding, through the top of a esterification column (400), the fatty acid (C) produced during the hydrolysis stage and transported by the first product line (5);
introducing, through the bottom of the esterification column (400), by means of a third supply line (10) from an external source, the reagent (R), so that in the presence of an impregnated heterogeneous catalyst (I) present inside the esterification column (400), an esterification reaction occurs and results in biodiesel (B) and water (A);

recycling the water (A) produced during the esterification reaction to the heat exchange device (100) through a second recycling line (9) at the top of the esterification column (400), where the water (A) is transformed into steam (V) and reintroduced into the hydrolysis column (200) along with the steam (V) coming from an external source; and removing the biodiesel (B) produced through the bottom of the esterification column (400) by means of a fourth product line (11).

2. The hydroesterification process for producing biodiesel from wet microalgae biomass according to claim 1, wherein the wet microalgae biomass (MU) used as feedstock is the result of a process of concentrating a cultivation of microalgae, preferably by centrifuging, producing at the end a wet microalgae biomass (MU) with a concentration in a range between 4% and 20%, and a lipid content in a range between 20% and 29%, based on a total weight of the wet microalgae biomass.

3. A hydroesterification process for producing biodiesel from wet microalgae biomass according to claim 1, wherein the reagent (R) used in the esterification reaction is methanol (M).

4. A hydroesterification process for producing biodiesel from wet microalgae biomass according to claim 1, wherein the hydrolysis of the wet microalgae biomass (MU) is done directly in the hydrolysis column (200), at a reaction temperature in a range between 180° C. and 300° C. for a time varying in the range between 0.5 and 2 hours.

5. A hydroesterification process for producing biodiesel from wet microalgae biomass according to claim 3, wherein the esterification reaction is carried out at a temperature varying in the range between 110° C. and 250° C., for a time varying in the range from 0.5 to 2 hours, the molar ratio between the methanol (M) and the fatty acids (C) being at a value varying in the range of 1.0 to 4.0 and the impregnated heterogeneous catalyst (I) present within the esterification column (400) is a catalyst of niobium oxide impregnated with phosphoric acid.

* * * * *